United States Patent [19]

Giordano et al.

[11] Patent Number: 5,023,365

[45] Date of Patent: Jun. 11, 1991

[54] PROCESS FOR PREPARING AN INTERMEDIATE

[75] Inventors: Claudio Giordano, Monza; Graziano Castaldi, Briona; Maurizio Paiocchi, Milan, all of Italy

[73] Assignee: Zambon Group S.p.A., Vicenza, Italy

[21] Appl. No.: 453,791

[22] Filed: Dec. 20, 1989

[30] Foreign Application Priority Data

Dec. 22, 1988 [IT] Italy ................................ 23054 A/88

[51] Int. Cl.$^5$ .............................................. C07C 69/76
[52] U.S. Cl. ....................................... 560/56; 562/401
[58] Field of Search ........................................... 560/56

[56] References Cited

FOREIGN PATENT DOCUMENTS 273316 7/1988 European Pat. Off. .

Primary Examiner—Paul J. Killos
Attorney, Agent, or Firm—Birch, Stewart, Kolasch & Birch

[57] ABSTRACT

A process is described for preparing an intermediate in the synthesis of naproxen.

The intermediate, namely the methyl ester of S(+)-2-(5-bromo-6-methoxy-2-naphthyl)-propionic acid or of its 5-chloro analogue, is prepared by preferential crystallization from mixtures with its enantiomer.

4 Claims, No Drawings

PROCESS FOR PREPARING AN INTERMEDIATE

This invention relates to a process for preparing the methyl ester of S(+)-2-(5-bromo-6-methoxy-2-naphthyl)-propionic acid or of the 5-chloro analogue, of formula

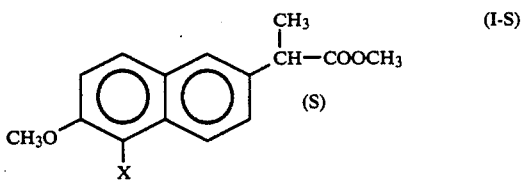

(in which X=Cl, Br)
starting from mixtures of I-S and I-R enantiomers in which the I-S isomer represents at least 90% of the mixture.

On dehalogenation and acid hydrolysis the I-S compound leads to the formation of S(+)-2-(6-methoxy-2-naphthyl)-propionic acid, a drug known as naproxen.

Most of the naproxen preparation processes comprise the synthesis of raceme mixtures of (R,S)-2-(6-methoxy-2-naphthyl)-propionic acid or its esters (such as European Pat. Nos. 35305 and 48136). The S(+) isomer isolated from the raceme mixture by a resolution process conducted with an optically active base such as cinchonidine, 1-phenyl-ethylamine or N-methyl-glucamine.

A process has also been described for preparing alkyl esters of S(+)-2-(6-methoxy-2-naphthyl)-propionic acid consisting of preferentially crystallizing the desired enantiomer, possibly under racemizing conditions, from a raceme mixture or from a mixture enriched in the desired enantiomer (U.S. Pat. No. 4,417,070).

The examples given in the aforesaid patent are limited to raceme mixtures with an enantiomeric R:S ratio of 1:1 and show appreciable results only when the crystallization is conducted twice or when conducted under racemizing conditions, i.e. in the presence of a base such as an alkaline alkoxide, an ammonium salt or a tertiary amine.

It is also necessary to use a quantity of the desired isomer to trigger the crystallization.

The reaction is conducted in inert solvents, preferably polar solvents such as methanol, ethanol and dimethylformamide.

The temperature is between −10° and 80° C.

The process of the present invention comprises preferential crystallization of the I-S compound from I-S and I-R mixtures in which the I-S enantiomer is present to the extent of at least 90%.

The process is implemented by cooling to 10°-20° C. a solution in methanol of I-S and I-R present in a ratio of greater than or equal to 90:10.

It would generally be expected that the crystallization of an enantiomeric mixture would provide a product rich in the predominant enantiomer.

In practive we have surprisingly found that the process of the present invention provides the I-S compound with very high yield and with enantiomeric purity.

Such results are not obtainable with an apparently very similar substrate such as the methyl ester of 2-(6-methoxy-2-naphthyl)-propionic acid, the enantiomers of which are indicated hereinafter as II-S and II-R.

By operating the process of the invention on an I-S/I-R mixture consisting of 90 parts of I-S (X=Br) and 10 parts of I-R, 83 parts of I-S are obtained with an enantiomeric excess (e.e.) of 98%, i.e. with an I-S/I-R ratio of 99:1.

Analogous results are obtained when X is chlorine in I-S.

However, the same procedure carried out on a mixture of II-S (90 parts) and II-R (10 parts) results in 72 parts of II-S being obtained with an e.e. of 92%.

If the process of the invention is carried out starting from a mixture of I-S (X=Br) (95 parts) and I-R (5 parts), 88 parts of I-S are obtained with an e.e. of 99.9%.

Analogous results are obtained when X is chlorine in I-S.

However, the same procedure carried out on a mixture of II-S (95 parts) and II-R (5 parts) results in 81 parts of II-S being obtained with an e.e. of 98.5%.

The process of the invention therefore provides the desired S isomer with unexpectedly high yields and equally unexpectedly high purity.

The starting substance for the process of the invention can be of various origins.

One of its direct sources is the enantioselective process described in European Pat. No. 158,913 (Zambon S.p.A.).

In one embodiment, the mixture of I-S and I-R in a ratio equal to or greater than 90:10 is dissolved in methanol to a concentration preferably of about 20% by weight.

The solution is cooled slowly and maintained at 10°-20° C., preferably 15° C., to complete the crystallization.

About 2-3 hours after the commencement of the operation the precipitate is filtered off, it having the yield and enantiomeric purity characteristics as stated heretofore.

Naproxen is prepared from the obtained I-S compound by a dehalogenation reaction of known type (such as for hydrogenolysis) and a likewise common acid hydrolysis reation.

The following examples are provided to better illustrate the invention.

EXAMPLE 1

Methyl ester of S(+)-2-(5-bromo-6-methoxy-2-naphthyl)-propionic acid

A sample (10 g) of the methyl ester of 2-(5-bromo-6-methoxy-2-naphthyl)-propionic acid having an S:R enantiomeric ratio of 90:10 (optical purity 80%) is dissolved in methanol (50 ml) while stirring at 65° C.

The solution is cooled gradually over 1 hour to +15° C. (at about 55° C. separation of crystals of the enantiomerically pure ester is observed), and the heterogeneous mixture is left stirring at 15° C. for 2 hours.

The suspension obtained in this manner is filtered, the precipitate washed with methanol (5 ml) and dried under vacuum at 55° C. to constant weight.

In this manner the analytically pure methyl ester of S(+)-2-(5-bromo-6-methoxy-2-naphthyl)-propionic acid is obtained, of M.P.=96.5°-97° C. and $[\alpha]_D^{20} = +55.3°$ (1% in chloroform), its optical purity being 98%.

The enantiomer ratio (99:1) was confirmed by $^1$H-NMR analysis (300 MHz) in CDCl$_3$ in the presence of europium (III) 3-(heptafluoropropyl)-hydroxymethylene-d-camphorate.

EXAMPLE 2

The procedure of Example 1 was repeated using the methyl ester of 2-(5-bromo-6-methoxy-2-naphthyl)-propionic acid in an I-S/I-R enantiomeric mixture of molar ratio 95:5.

The product obtained has an optical purity of 99.9%. $[\alpha]_D^{20} = +56.5°$.

EXAMPLE 3

The procedure of Example 1 was repeated using the methyl ester of 2-(5-chloro-6-methoxy-2-naphthyl)-propionic acid in an I-S/I-R enantiomeric mixture of molar ratio 95:5.

The product obtained has the following characteristics: M.P. = 107° C., $[\alpha]_D^{20} = +64.6°$ (1% in CHCl$_3$), optical purity = 99.9%, yield = 85%.

We claim:

1. A process for preparing the methyl ester of S(+)-2-(5-bromo-6-methoxy-2-naphthyl)-propionic acid or of the 5-chloro analogue (I-S compounds), consisting of subjecting to preferential crystallization a mixture of I-S and its I-R enantiomer in a ratio greater than or equal to 90:10 by dissolving it in methanol and cooling to a temperature of between 10° and 20° C.

2. A process as claimed in claim 1, wherein the temperature is 15° C.

3. A process as claimed in claim 1, wherein the initial concentration of the methanolic solution is 20% by weight.

4. A process as claimed in claim 1, wherein a mixture of the I-S and I-R enantiomers in a ratio greater than or equal to 90:10 is dissolved in methanol to a concentration of 20% by weight, the temperature is adjusted slowly to 15° C., the I-S enantiomer is allowed to precipitate and is separated by filtration.

* * * * *